United States Patent [19]

Schwartz et al.

[11] Patent Number: 5,089,416
[45] Date of Patent: Feb. 18, 1992

[54] METHOD OF USE OF NON-FLUORESCENT PARTICLES TO DETERMINE FLUORESCENCE THRESHOLD OF A FLOW CYTOMETER RELATIVE TO THE AUTOFLUORESCENCE OF SAMPLES

[75] Inventors: Abraham Schwartz; Emma Fernandez-Repollet, both of Hato Rey, P.R.

[73] Assignee: Caribbean Microparticles Corporation, Hato Rey, P.R.

[21] Appl. No.: 620,530

[22] Filed: Nov. 21, 1990

Related U.S. Application Data

[63] Continuation-in-part of Ser. No. 374,435, Jun. 30, 1989, which is a continuation-in-part of Ser. No. 128,786, Dec. 4, 1987, Pat. No. 4,857,451, which is a continuation-in-part of Ser. No. 805,654, Dec. 11, 1985, Pat. No. 4,774,189, which is a continuation-in-part of Ser. No. 685,464, Dec. 24, 1984, Pat. No. 4,767,206.

[51] Int. Cl.$^5$ .................. G01N 31/00; G01N 33/48; G01J 1/02
[52] U.S. Cl. ................................. 436/8; 436/10; 435/967; 356/42; 356/243
[58] Field of Search ........... 436/8, 10, 15; 435/967; 356/42, 243

[56] References Cited

U.S. PATENT DOCUMENTS

| | | | |
|---|---|---|---|
| 4,035,316 | 7/1977 | Yen | 260/2.5 B |
| 4,157,323 | 6/1979 | Yen | 260/29.7 M |
| 4,162,282 | 7/1979 | Fulwyler | 264/9 |
| 4,247,434 | 1/1981 | Vanderhoff | 260/29.6 RB |
| 4,254,096 | 3/1981 | Monthony | 424/8 |
| 4,438,239 | 3/1984 | Rembaum | 525/54.1 |
| 4,511,662 | 4/1985 | Baran | 436/513 |
| 4,552,633 | 11/1985 | Kumakura | 204/159.21 |
| 4,605,630 | 8/1986 | Kung | 436/511 |
| 4,609,689 | 9/1986 | Schwartz | 523/202 |
| 4,656,144 | 4/1987 | Hosaka | 436/534 |
| 4,665,020 | 5/1987 | Saunders | 435/7 |
| 4,694,035 | 9/1987 | Kasai | 524/458 |
| 4,698,262 | 10/1987 | Schwartz | 428/402 |
| 4,699,826 | 10/1987 | Schwartz | 428/402 |
| 4,699,828 | 10/1987 | Schwartz | 428/402 |
| 4,714,682 | 12/1987 | Schwartz | 436/10 |
| 4,751,188 | 6/1988 | Valet | 436/63 |
| 4,767,206 | 8/1988 | Schwartz | 356/73 |
| 4,774,189 | 9/1988 | Schwartz | 436/10 |
| 4,828,984 | 5/1989 | Schwartz | 435/7 |
| 4,857,451 | 8/1989 | Schwartz | 435/7 |
| 4,867,908 | 9/1989 | Recktenwald et al. | 436/10 |
| 4,868,126 | 9/1989 | Schwartz | 436/10 |
| 4,918,004 | 4/1990 | Schwartz | 435/7 |

*Primary Examiner*—David L. Lacey
*Assistant Examiner*—William K. Y. Chan
*Attorney, Agent, or Firm*—Olive & Olive

[57] ABSTRACT

A qualitative and quantitative method of determining the fluorescence threshold of an instrument and of determining whether the instrument is sensitive enough to measure the autofluorescence of a sample. The method utilizes non-fluorescent particles such a microbeads which are run on a flow cytometer. The peak channel position of the microbeads is used as the fluorescence threshold.

10 Claims, 1 Drawing Sheet

METHOD OF USE OF NON-FLUORESCENT PARTICLES TO DETERMINE FLUORESCENCE THRESHOLD OF A FLOW CYTOMETER RELATIVE TO THE AUTOFLUORESCENCE OF SAMPLES

CROSS-REFERENCE TO RELATED APPLICATIONS

This application is a continuation-in-part of U.S. application Ser. No. 07/374,435 filed June 30, 1989, which in turn is a continuation-in-part of U.S. application Ser. No. 07/128,786 filed Dec. 4, 1987, issued Aug. 15, 1989 as U.S. Pat. No. 4,857,451, which in turn is a continuation-in-part of U.S. application Ser. No. 06/805,654 filed Dec. 11, 1985, issued Sept. 27, 1988 as U.S. Pat. No. 4,774,189, which in turn is a continuation-in-part of U.S. application Ser. No. 06/685,464 filed Dec. 24, 1984, issued Aug. 30, 1988, as U.S. Pat. No. 4,767,206.

BACKGROUND OF THE INVENTION

1. Field of the Invention

This invention relates generally to the method of determining the fluorescence threshold (noise level) of a flow cytometer relative qualitatively to the autofluorescence of cells and quantitatively in terms of the calibration units of molecules of equivalent soluble fluorochromes (MESF) using calibrated fluorescent microbead standards.

2. Description of the Related Art

Flow cytometers are used to analyze biological cells and particles in a fluid sample by intersecting a thin stream of fluid by an illumination source, usually a laser beam. The resulting forward and right angle scatter, and fluorescent light is analyzed with photomultiplier tubes (PMTs). The fluorescence channels of a flow cytometer, designated by FL1, FL2, FL3, etc. are each set with barrier filters to detect the selected specific dye while filtering out signals from other wavelengths.

In practice, however, these filters are not 100% effective in filtering out signals from other wavelengths and optical noise can arise from imperfections in the filters, pin-holes in the coatings, coating which themselves fluoresce, etc. Filters which are coated must be placed in the optical path such that the coating faces the correct direction, or else fluorescence from the coating will be passed along to the PMTs. In addition, small portions of the illumination source may be non-specifically scattered within the instrument and register in the PMTs due to the geometry of the instrument and optical path. These are some, but not all the optical sources of fluorescence noise which can reach the PMT as a signal.

Another source of noise resulting in a fluorescence signal comes the electronics of the flow cytometer, including, but not limited to, signal processors, the amplifiers, and the power source.

Measurements of all the parameters (forward scatter, side scatter, FL1, FL2, etc.) of individual cells or particles are taken when the instrument is triggered in a particular channel, usually the forward scatter. If a non-fluorescent particle triggers the forward scatter channel, theoretically, the instrument will be taking readings in the fluorescence channels (FL1, FL2, etc.) which are not from the particles themselves, but rather from the noise in each channel.

These sources of noise will be additive and the fluorescence threshold level of a particular fluorescence channel will be the summation of the optical and electronic noise, below which a fluorescence signal from a sample will not be possible to measure on that particular instrument.

Biological cells and many other particles have intrinsic fluorescence referred to as autofluorescence. Autofluorescence arises from fluorescent compounds or impurities within the cells or particles. For example, most mammalian cells contain riboflavins and other compounds which are naturally fluorescent and give the cell some level of autofluorescence. Many cells in tissue culture have higher levels of autofluorescence than those occurring in living tissue.

The level of autofluorescence of cells or particles can be measured by calibrating the particular fluorescence channel of interest in terms of MESFs and reading the value from the calibration plots as described in U.S. Pat. Nos. 4,714,682; 4,767,206; 4,774,189 and 4,857,451. The disclosure of all patents and patent applications cited herein including those referred to in the Cross-Reference to Related Applications, is hereby incorporated herein by reference.

Calibration of fluorescent microbead standards is provided by means of the invention of U.S. Pat. No. 4,714,682 which relates a microbead standard back to a stable and reproducible solution of primary standard which has the same excitation and emission spectra as the sample being measured. With sufficiently dilute solutions, considerations of quenching and changes of extinction coefficient may be avoided, as long as the spectra of the primary soluble standard solution, the microbead standards, and the labeled cells in the sample are the same. Thus, fluorescent intensities of a sample may be related to a quantitative concentration of a soluble primary standard via calibrated microbeads which have the same spectra.

As discussed in U.S. Pat. No. 4,714,682, fluorescenated microbeads may be calibrated with such a system in terms of Equivalent Soluble Dye Molecules per Microbead. For example, fluorescein microbeads are standardized against a primary laser grade fluorescein, which laser grade is stable, and of the highest purity of any of the fluorescein compounds and has excitation and emission spectra equivalent to that of FITC-labeled cells and the fluorescein microbead standards. The fluorescent microbead standards are calibrated by determining the fluorescent intensity of standard solutions of laser grade dyes with a fluorometer and relating those fluorescence intensities to the fluorescence intensity of suspensions of the microbeads. The number of microbeads in the suspension per unit volume is determined with a Coulter Counter™ or a Hemocytometer™. Then from these data, the number of equivalent soluble dye molecules per microbead is calculated by dividing the equivalent soluble dye molecules per unit volume by the number of microbeads per that unit volume.

In co-pending application Ser. No. 07/374,435, the compensation circuits are adjusted such that the level of fluorescence in the fluorescence channels, other than the channel designated for particular fluorescent dye (the primary channel(s)), is equal to the level of fluorescence of the sample prior to labeling the sample with fluorescent dyes. Autofluorescent microbeads, matching the fluorescence spectra and intensity of the unlabeled, naturally fluorescent sample to be measured, are run on the flow cytometer in the FL1 versus FL2 fluorescence channel dot plot or histogram display mode.

The previous methods do not provide for qualitative method for determining machine sensitivity, and require use of quantitative standards and use of a calibration curve without providing information o the machine noise and sample autofluorescence.

It is therefore an object of the invention to provide a method of use of non-fluorescent particles to determine fluorescence threshold of a flow cytometer relative to the autofluorescence of samples.

Other objects and advantages of the invention will be more fully apparent from the following disclosure and appended claims.

SUMMARY OF THE INVENTION

This invention involves both a qualitative and a quantitative method of determining the fluorescence threshold (noise level) of an instrument, and if the instrument is sensitive enough to measure the autofluorescence of a sample. In turn, knowing the autofluorescence of the sample will give the basis for setting the level of positive labeling of specific markers, e.g., labeling of low density antigens on cell surfaces.

The qualitative method of the invention involves adjusting the instrument such that the autofluorescence of the sample is visible on the fluorescence histogram, and then at the same instrument settings, analyzing a population of non-fluorescent particles and determining their fluorescence level relative to the autofluorescence of the sample. Preferably, the non-fluorescent particles are microbeads as described in the cited patents on microbeads. If the non-fluorescent microbeads appear in a channel lower than the sample, then the autofluorescence from the sample is above the instrument noise and is a fluorescence signal readable on the instrument. It is not necessary to determine the actual noise level of the particular fluorescence channel in terms of MESFs, as long as it is known that the fluorescence signal from the sample is above the noise level of the instrument.

However, if the noise level of the instrument is equal to or higher than the autofluorescence of the sample, then the fluorescence level of the sample and the non-fluorescence particles will coincide on the histogram. In this case, it is necessary to determine the noise level of the instrument quantitatively in MESFs to determine how much higher the noise level is above autofluorescence of the sample.

DETAILED DESCRIPTION OF THE INVENTION, AND PREFERRED EMBODIMENTS THEREOF

Figure 1:
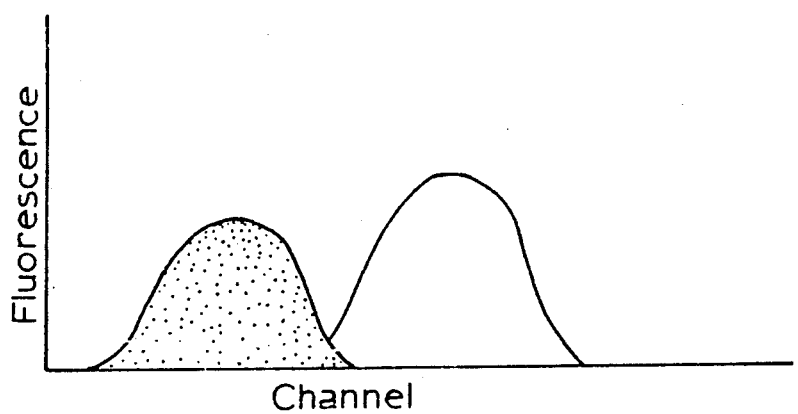
FIG. 1 is a histogram of a fluorescence channel where the peak channel of the non-fluorescent particles (dotted area) is below the peak channel of the autofluorescence of the sample (undotted area) indicating that the fluorescence threshold of the instrument is low enough to determine the actual autofluorescence of the sample.

The invention is a method of determining fluorescence threshold of a flow cytometer, comprising
  (a) providing a population of non-fluorescent particles having a coefficient of variation of diameter of about 2 percent or less;
  (b) running said population of non-fluorescent particles on said flow cytometer and determining the channel position of said population on said flow cytometer; and
  (c) using said channel position as the fluorescence threshold.

When a sample is used, the method of using non-fluorescent particles to determine fluorescence threshold of a flow cytometer relative to autofluorescence of samples, comprises:
  (a) adjusting the flow cytometer setting and filters so that the fluorescence signal of the sample is visible on the fluorescence histogram in a specific fluorescence channel;
  (b) providing a population of non-fluorescent particles having a coefficient of variation of diameter of about 2 percent or less;
  (c) running said non-fluorescent particle population on said flow cytometer without changing any flow cytometer settings;
  (d) determining the fluorescence threshold of the flow cytometer by determining the channel position of the non-fluorescent particle population;
  (e) determining if the fluorescence threshold of the flow cytometer is less than the fluorescence signal of the sample; and
  (f) if the fluorescence threshold of the flow cytometer coincides with the fluorescence level of the sample, then the fluorescence threshold is equal to or greater than the fluorescence of the sample, making it necessary to quantitatively determine the fluorescence threshold of the instrument in molecules of equivalent soluble fluorochromes using calibrated fluorescent microbead standards.

The preferred non-fluorescence particles used to determine the fluorescence threshold (noise level) of a flow cytometer are highly uniform microbeads, in which the coefficient of variation (CV) of the diameter is <2%, and which are comprised of polymeric materials which do not have any intrinsic fluorescence. Such polymeric materials include, but are not limited to, polystyrene, polymethyl methacrylate, polyvinytoluene, etc., with the preferred polymeric material being polymethyl methacrylate. The size of the highly uniform microbeads should be such that they give a forward scatter signal close to that obtained by the sample so that the sample and microbeads appear to be the same size.

The non-fluorescent particles used in the invention may be made as described in U.S. Pat. Nos. 4,714,682; 4,767,206; 4,774,189; and 4,918,004 and prior copending applications Ser. No. 07/374,435 with the primary prerequisites being that no fluorescent dye is added to the beads and that the beads have a high uniformity in size.

Examples of the quantitative fluorescence standards in which their fluorescence spectra match those of the fluorescence label used on the sample, are described in U.S. Pat. Nos. 4,767,206; 4,774,189; and 4,918,004 and U.S. patent application Ser. No. 07/465,792, commonly assigned.

Figure 3:
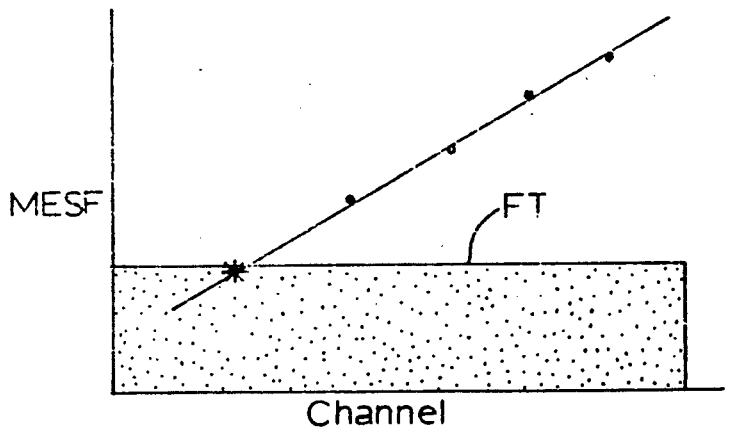
FIG. 3 is a calibration plot in which the fluorescence threshold (FT) of the instrument is determined by the non-fluorescent particle. Calibrated microbead MESF is indicated by (11) and the non-fluorescent particle MESF is indicated by (*).

The preferred method of use in this invention is to set the instrument such that it can observe the autofluorescence of the sample in a specific fluorescence channel using appropriate filters, and then run the non-fluorescent microbeads at the same instrument settings and determine if the non-fluorescent microbeads appear less fluorescent (i.e., in a low channel) than the sample (FIG. 1). If this is the case, it may be concluded that the observed autofluorescence level of the sample is real and above the fluorescence threshold of the instrument. The fluorescence threshold of the instrument can be quantitatively determined by calibrating the instrument at these particular instrument settings with calibrated microbead standards as described, for example, in U.S. Pat. Nos. 4,767,206 and 4,774,189, and determining where the non-fluorescent microbeads fall on the calibration plot and reading the corresponding MESF value. FIG. 3 shows a calibration plot with the fluorescent threshold indicated.

Figure 2:
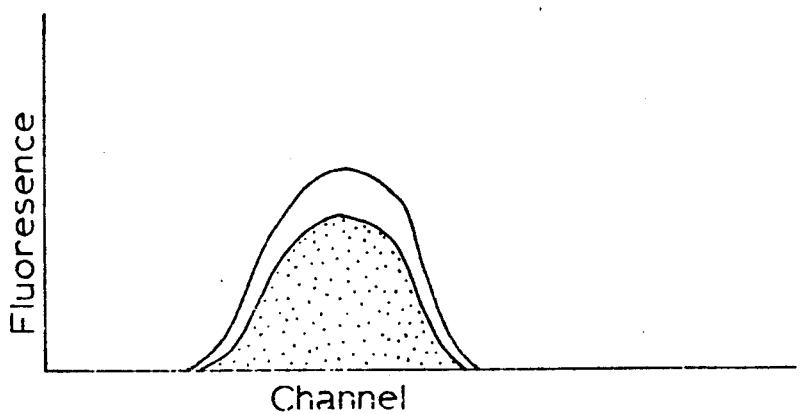
FIG. 2 is a histogram of the fluorescence channel where the peak channel of the non-fluorescent particles (dotted area) coincides with the peak channel of the fluorescence level of the sample (undotted area indicating that the fluorescence threshold of the instrument is equal to or higher than the autofluorescence level of the sample.

If the non-fluorescent microbeads coincide with the autofluorescence of the sample, this indicates that the noise level of the instrument is either equal to o greater than the autofluorescence level of the sample (FIG. 2). Such a situation may cause inaccuracies in determining low level labeling of the samples because the labeling may be obscured by the instrument noise. Therefore, the noise level of the instrument should be determined by the methods described above, so as to find where the autofluorescence of the sample is compared to the instrument noise. For example, if the instrument has a noise level of 5000 MESFs and the autofluorescence level of the sample is 1000 MESF, as is the case with peripheral lymphocytes, then any low level labeling with antibodies resulting in fluorescence intensities between 1000-5000 MESF will not be seen by the instrument.

The features and advantages of the present invention will be more clearly understood by reference to the following examples, which are not to be construed as limiting the invention.

EXAMPLE I

A FACScan flow cytometer (Becton Dickinson Immunocytometry Systems, Orangeburg, N.Y.) is adjusted such that the peak channel of the population of lymphocytes obtained from lysed whole human peripheral blood appear in the FL1 channel 86 on a scale of 1024 channels (PMT=620 v). When 8.0μ non-fluorescent microbeads are analyzed under the same instrument settings, their peak channel is off scale to the left of the lymphocytes. This indicates that the instrument has a fluorescence threshold (noise level) below that of the autofluorescence of the lymphocytes.

EXAMPLE II

The FL1 PMT voltage was increased to 700 volts for the instrument in Example I, and the peak channel of autofluorescence of the sample (which is the same sample as used in Example I) fell in channel 259. The peak channel of the non-fluorescent microbeads fell in channel 124. Again, this indicated that the fluorescence threshold of the instrument was below the autofluorescence of the lymphocytes.

EXAMPLE III

A set of calibrated fluorescein standard microbeads (9,600-500,000 MESF) were run on the instrument at the setting in Example II and a calibration plot was made using linear regression of the MESF values of the beads plotted against the channel. The fluorescence threshold is the channel position of the non-fluorescent microbeads and with the sample autofluorescence may be taken from the calibration plot. In this example, the fluorescence threshold was determined to be 214 MESF and the autofluorescence of the lymphocytes was determined to be 898 MESF. This shows that the instrument was sensitive enough to measure the real autofluorescence of the sample.

EXAMPLE IV

A whole lysed peripheral blood sample was run on a FACS Analyzer (Becton Dickinson Immunocytometry Systems, Orangeburg, N.Y.) and the autofluorescence peak of the lymphocytes was placed in channel 27 (scale 256). The 8.0μ non-fluorescent microbeads also had their peak in the same position, channel 27. This indicated that the fluorescence threshold (noise level) was equal or higher than the autofluorescence of the cells.

EXAMPLE V

The FACS Analyzer in Example IV was calibrated using the calibrated fluorescein microbead standards in Example III and the fluorescence threshold of the instrument was determined to be 4840 MESF. This noise level is much higher than the autofluorescence level of the lymphocytes as determined in Example III, which was 898 MESF.

While the invention has been described with reference to specific embodiments thereof, it will be appreciated that numerous variations, modifications and embodiments are possible, and accordingly, all such variations, modifications and embodiments are regarded as being within the spirit and scope of this invention.

What is claimed is:

1. A method of determining fluorescence threshold of a flow cytometer, comprising:
   (a) running a selected autofluorescent sample on said flow cytometer;
   (b) determining a flow cytometer setting where sample autofluorescence is observable;
   (c) providing a population of non-fluorescent particles;
   (d) running said population of non-fluorescent particles on said flow cytometer at the flow cytometer setting where autofluorescence of the selected sample is observable;
   (e) determining a peak channel position of said population on said flow cytometer; and
   (f) using said peak channel position as a fluorescence threshold for determining whether the sample autofluorescence is real.

2. A method of determining fluorescence threshold of a flow cytometer according to claim 1, wherein the non-fluorescent particles comprise microbeads having a coefficient of variation of diameter of about 2 percent or less.

3. A method of determining fluorescence threshold of a flow cytometer according to claim 2, wherein the microbeads are made of polymethyl methacrylate.

4. A method of determining fluorescence threshold of a flow cytometer according to claim 2, wherein the microbeads are made of polystyrene.

5. A method of determining fluorescence threshold of a flow cytometer according to claim 2, wherein the microbeads are made of polyvinyltoluene.

6. A method of using non-fluorescent particles to determine fluorescence threshold of a flow cytometer relative to autofluorescence of samples, comprising:
   (a) running a sample having a fluorescence signal on said flow cytometer;
   (b) adjusting flow cytometer settings and filters so that the fluorescence signal of the sample is visible on a fluorescence histogram of the flow cytometer in a specific fluorescence channel;
   (c) providing a population of non-fluorescent particles;
   (d) running said non-fluorescent particle population on said flow cytometer without changing any flow cytometer settings; and
   (e) determining the fluorescence threshold of the flow cytometer by determining a peak channel position of the non-fluorescent particle population; wherein when the fluorescence threshold of the flow cytometer is less than the fluorescence signal of the sample, then the fluorescence signal from the sample is real and not instrument noise; and when the fluorescence threshold of the flow cytometer coincides with the fluorescence level of the sample, then the fluorescence threshold is equal to or greater than the fluorescence of the sample, and the fluorescence threshold of the instrument being quantitatively determined in molecules of equivalent soluble fluorochromes using calibrated fluorescent microbead standards.

7. A method of using non-fluorescent microbeads according to claim 6, wherein the samples are lymphocytes and the diameter of the microbeads is about 8 micron.

8. A method of using non-fluorescent microbeads according to claim 6, wherein the microbeads are made of polymethyl methacrylate.

9. A method of using non-fluorescent microbeads according to claim 6, wherein the microbeads are made of polystyrene.

10. A method of using non-fluorescent microbeads according to claim 6, wherein the microbeads are made of polyvinyltoluene.

* * * * *